United States Patent [19]

Hansen et al.

[11] 4,249,933
[45] Feb. 10, 1981

[54] HERBICIDAL AGENTS CONTAINING A THIOLCARBAMATE

[75] Inventors: Hanspeter Hansen, Ludwigshafen; Karl Eicken, Wachenheim; Bruno Wuerzer, Limburgerhof, all of Fed. Rep. of Germany

[73] Assignee: BASF Aktiengesellschaft, Fed. Rep. of Germany

[21] Appl. No.: 58,259

[22] Filed: Jul. 17, 1979

[30] Foreign Application Priority Data

Jul. 27, 1978 [DE] Fed. Rep. of Germany ....... 2832974

[51] Int. Cl.$^3$ ............................................ A01N 25/32
[52] U.S. Cl. ......................................... 71/88; 71/100; 71/118
[58] Field of Search ............................ 71/88, 118, 100

[56] References Cited

U.S. PATENT DOCUMENTS

| | | | |
|---|---|---|---|
| 3,742,007 | 6/1973 | Osieka et al. ................. | 71/100 X |
| 3,989,503 | 11/1976 | Pallos et al. ................... | 71/88 |
| 4,021,224 | 5/1977 | Pallos et al. ................... | 71/88 |

*Primary Examiner*—Catherine L. Mills
*Attorney, Agent, or Firm*—Keil & Witherspoon

[57] ABSTRACT

Herbicidal agents containing ethyl-N-ethyl-N-bicyclo-[2.2.1]-hept-2-yl-thiolcarbamate of the formula

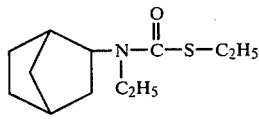

as herbicidal active ingredient and at least one haloacylamide of the formula

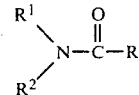

where R denotes linear or branched haloalkyl of a maximum of 3 carbon atoms, and $R^1$ and $R^2$ are identical or different and each denotes linear or branched alkyl of a maximum of 6 carbon atoms which is unsubstituted or substituted by alkoxy of a maximum of 4 carbon atoms or by cyano, $R^1$ and $R^2$ further denote cycloalkyl of 3 to 6 carbon atoms, or linear or branched alkenyl or alkynyl of a maximum of 4 carbon atoms, or $R^1$ and $R^2$, together with the nitrogen atom whose substituents they are, form a 4- to 9-membered, saturated monocyclic or bicyclic ring which is unsubstituted or mono- or polysubstituted by linear or branched alkyl of a maximum of 4 carbon atoms, or a tetrahydro-1,3-oxazine ring of the formula

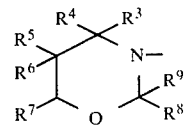

where $R^3$, $R^4$, $R^5$, $R^6$ and $R^7$ are identical or different and each denotes hydrogen or linear or branched alkyl of a maximum of 3 carbon atoms, $R^8$ denotes hydrogen or linear or branched alkyl of a maximum of 8 carbon atoms, $R^9$ denotes hydrogen, linear or branched alkyl of a maximum of 8 carbon atoms, alkoxyalkyl of a maximum of 6 carbon atoms or dialkoxyalkyl of a maximum of 8 carbon atoms, or $R^8$ and $R^9$ may together form a methylene chain of 4 or 5 carbon atoms, as antagonistic agent.

The weight ratio of ethyl-N-ethyl-N-bicyclo-[2.2.1]-hept-2-yl-thiolcarbamate to antagonistic agent is, whether applied together or separately, from 1:1 to 1:0.01.

7 Claims, No Drawings

HERBICIDAL AGENTS CONTAINING A THIOLCARBAMATE

The present invention relates to herbicidal agents containing a thiolcarbamate as herbicidal active ingredient and haloacylamides as antagonistic agents, and a process for the selective control of unwanted plants with these herbicidal agents.

German Laid-Open Application DE-OS No. 1,953,262 discloses that ethyl-N-ethyl-N-bicyclo-[2.2.1]-hept-2-yl-thiolcarbamate is effective as a selective herbicide, predominantly in sugarbeets. The active ingredient has a very good herbicidal action on numerous monocotyledonous and dicotyledonous unwanted plants. It is suitable for combating weeds in Indian corn if the selectivity range is increased somewhat. By this is meant the range in application rate which on the one hand is necessary for a good herbicidal action and on the other is only just tolerated by the crop plants without damage being caused.

Further, it is disclosed in German Laid-Open Application DE-OS No. 2,218,097 that haloacetamides, when used in combination with herbicidal thiolcarbamates, improve the tolerance of these active ingredients by certain crops.

We have now found that herbicidal agents containing ethyl-N-bicyclo-[2.2.1]-hept-2-yl-thiolcarbamate of the formula

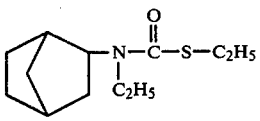

as herbicidal active ingredient and at least one haloacylamide of the formula

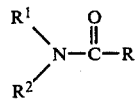  I, where R denotes linear or branched haloalkyl of a maximum of 3 carbon atoms, and $R^1$ and $R^2$ are identical or different and each denotes linear or branched alkyl of a maximum of 6 carbon atoms which is unsubstituted or substituted by alkoxy of a maximum of 4 carbon atoms or by cyano, $R^1$ and $R^2$ further denote cycloalkyl of 3 to 6 carbon atoms, or linear or branched alkenyl or alkynyl of a maximum of 4 carbon atoms, or $R^1$ and $R^2$, together with the nitrogen atom whose substituents they are, form a 4- to 9-membered, saturated monocyclic or bicyclic ring which is unsubstituted or mono- or polysubstituted by linear or branched alkyl of a maximum of 4 carbon atoms, or a tetrahydro-1,3-oxazine ring of the formula

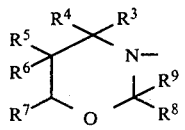

where $R^3$, $R^4$, $R^5$, $R^6$ and $R^7$ are identical or different and each denotes hydrogen or linear or branched alkyl of a maximum of 3 carbon atoms, $R^8$ denotes hydrogen or linear or branched alkyl of a maximum of 8 carbon atoms, $R^9$ denotes hydrogen, linear or branched alkyl of a maximum of 8 carbon atoms, alkoxyalkyl of a maximum of 6 carbon atoms or dialkoxyalkyl of a maximum of 8 carbon atoms, or $R^8$ and $R^9$ may together form a methylene chain of 4 or 5 carbon atoms, as antagonistic agent, are much better tolerated by crop plants such as Indian corn than herbicidal agents containing ethyl-N-ethyl-N-bicyclo-2.2.1-hept-2-yl-thiolcarbamate without an antagonistic agent. The good herbicidal action of the thiolcarbamate is unimpaired.

The antagonistic compounds of the formula I themselves have scarcely any influence, if at all, on germination and growth of crop and unwanted plants, even at application rates well above those required for an antagonistic effect. However, they are capable of considerably reducing the phytotoxicity of the thiolcarbamate to crop plants such as Indian corn, or of eliminating it completely.

Suitable antagonistic haloacylamides are compounds of the formula I in which R is haloalkyl, especially chloroalkyl, e.g., chloromethyl, dichloromethyl, trichloromethyl and 2-chloroethyl, especially dichloromethyl.

The substituents $R^1$ and $R^2$ may be identical or different and denote linear or branched alkyl of a maximum of 6 carbon atoms, e.g., methyl, ethyl, n-propyl, isopropyl, n-butyl, isobutyl, sec-butyl, tert-butyl, n-hexyl, and 1,4-dimethyl-n-butyl, linear or branched alkenyl or alkynyl of a maximum of 4 carbon atoms, e.g., allyl, propargyl, and 1-methylbutyn-2-yl, or cycloalkyl of 3 to 6 carbon atoms, e.g., cyclopropyl and cyclohexyl. The alkyl radicals are unsubstituted or substituted by alkoxy of a maximum of 4 carbon atoms, e.g., methoxy and ethoxy, or by cyano. The alkoxy group is preferably in the terminal position to the carbon radicals.

$R^1$ and $R^2$ may also, together with the nitrogen atom whose substituents they are, form a 4- to 9-membered, saturated mono- or bicyclic ring. This heterocycle is unsubstituted or mono- or polysubstituted by linear or branched alkyl of a maximum of 4 carbon atoms. Examples of such rings are piperidinyl, alkylpiperidinyl, e.g., 3,5-diethylpiperidinyl, 2,5-dimethylpyrrolidinyl, azetidinyl, alkylazetidinyl, e.g., 2.2.4-trimethylazetidinyl, hexahydroazepinyl, alkylhexahydroazepinyl, e.g., 3.5.5/3.3.5-trimethylhexahydroazepinyl and 2,3-dimethylhexahydroazepinyl, aza-bicyclo-[3.2.2]-nonyl, alkyl-aza-bicyclo-octyl, e.g., trimethyl-aza-bicyclo-[3.2.1]-octyl, and aza-bicyclo-[3.2.0]-heptyl.

Further, $R^1$ and $R^2$ may, together with the nitrogen atom whose substituents they are, form a tetrahydro-1,3-oxazine ring of the formula

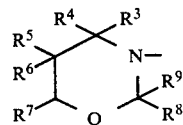

The substituents $R^3$ to $R^7$ may be identical or different and denote hydrogen or alkyl of a maximum of 3 carbon atoms, especially hydrogen and methyl. $R^8$ and $R^9$ denote hydrogen or alkyl of a maximum of 8 carbon atoms, such as methyl, ethyl, n-propyl, isopropyl, butyl, hexyl, heptyl and octyl.

$R^9$ may also denote alkoxyalkyl of a maximum of 6 carbon atoms or dialkoxyalkyl of a maximum of 8 carbon atoms, e.g., methoxymethyl and dimethoxymethyl. $R^8$ and $R^9$ may together form a methylene chain with 4 or 5 carbon atoms. R denotes haloalkyl of a maximum of 3 carbon atoms, preferably chloroalkyl, especially chloromethyl and dichloromethyl. These N-haloacetamide-tetrahydro-1,3-oxazines are new.

Haloacylamides of the formula I preferred as antagonists are N-isopropyl-N-propargyldichloroacetamide, N-dichloroacetyl-4,4-dimethyltetrahydro-1,3-oxazine, N-dichloroacetyl-4,4,6-trimethyltetrahydro-1,3-oxazine, and N,N-diallyldichloroacetamide.

The haloacylamides of the formula I may be obtained by reaction of amines of the formula $$\begin{array}{c} R^1 \\ \diagdown \\ NH, \\ \diagup \\ R^2 \end{array}$$

where $R^1$ and $R^2$ have the above meanings, with haloacetyl chloride. The reaction is carried out in conventional manner in the presence of an agent which binds hydrogen chloride, in an inert solvent or diluent.

The following examples illustrate the manufacture of the haloacylamides.

EXAMPLE 1

118 g of isopropylpropargylamine and 123 g of triethylamine are dissolved in 670 ml of toluene. While cooling and at room temperature, a solution of 180 g of dichloroacetyl chloride in 450 ml of toluene is dripped into this solution. The mixture is allowed to react for 1 hour before being filtered, and the filtrate is washed with water. The residue remaining after removal of the solvent is washed with petroleum ether. There is obtained 214 g (84% of theory) of N-isopropyl-N-propargyldichloroacetamide; b.p. (0.013 mbar):80°–82° C.; m.p.: 58°–59° C.

EXAMPLE 2

At $-10°$ C. and while stirring, 23.2 parts by weight of dichloroacetyl chloride in 100 parts by volume of toluene is dripped into 23.0 parts by weight of 4,4-dimethyltetrahydro-1,3-oxazine and 20.7 parts by weight of triethylamine in 100 parts by volume of toluene. After the mixture has been stirred for 2 hours at room temperature, there are added 150 parts by volume of methylene chloride and sufficient water to form 2 clear phases. The organic phase is separated and washed twice, each time with 50 parts by volume of water. After drying and evaporation of the solvents under reduced pressure, there is isolated 41 parts by weight of N-dichloroacetyl-4,4-dimethyltetrahydro-1,3-oxazine of melting point 105°–106° C., which melts, after recrystallization from methanol, at 106°–107° C.

$C_8H_{13}N_2O_2Cl_2$ MW 226 calc.: C 42.5 H 5.8 N 6.19. found: C 42.6 H 5.8 N 6.2.

The following compounds may be prepared analogously:

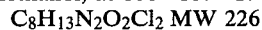

| $R^1$ | $R^2$ | b.p./m.p./$n_D$ | | |
|---|---|---|---|---|
| $CH_2=CH-CH_2-$ | $CH_2=CH-CH_2-$ | $n_D^{30}$: | 1.4990 | |
| $HC\equiv C-CH_2-$ | $n-C_3H_7$ | $n_D^{26}$: | 1.4978 | |
| $HC\equiv C-CH_2-$ | $(CH_3)_2CH-CH_2-CH(CH_3)-$ | $n_D^{25}$: | 1.4889 | |
| $HC\equiv C-CH_2-$ | $CH_3$ | $n_D^{25}$: | 1.5090 | |
| $i-C_3H_7$ | $C_2H_5$ | $n_D^{25}$: | 1.4849 | |
| $i-C_3H_7$ | $i-C_3H_7$ | m.p.: | 62–65° C. | |
| $n-C_4H_9$ | $C_2H_5$ | $n_D^{25}$: | 1.4802 | |
| sec.-$C_4H_9$ | $CH_3$ | $n_D^{25}$: | 1.4820 | |
| $i-C_4H_9$ | $CH_3$ | $n_D^{25}$: | 1.4820 | |
| sec.-$C_4H_9$ | $HC\equiv C-CH(CH_3)-$ | $n_D^{25}$: | 1.4923 | |
| $n-C_4H_9$ | $CH_3$ | $n_D^{25}$: | 1.4835 | |
| $HC\equiv C-CH_2-$ | sec.-$C_4H_9$ | $n_D^{25}$: | 1.4960 | |
| | $-(CH_2)_3-$ | m.p.: | 37–39° C. | |
| | $-(CH_2)_4-$ | $n_D^{25}$: | 1.5190 | |
| | $-(CH_2)_5-$ | m.p.: | 41–42° C. | |
| | $-CH_2-CH-(CH_2)_2-CH-CH_2-$ $\diagdown\ \diagup$ $CH_2-\!\!\!-CH_2$ | m.p.: | 101–102° C. | |
| | $-CH(CH_3)-CH_2-C(CH_3)_2-$ | m.p.: | 48–49° C. | |
| | $-CH_2-CH(CH_3)-CH_2-C(CH_3)_2-CH_2-CH-$ $\diagdown\qquad\qquad\diagup$ $CH_2$ | m.p.: | 82–84° C. | |
| | $-CH(CH_3)-(CH_2)_2-CH(CH_3)-$ | m.p.: | 61–65° C. | |
| | $-CH_2-CH(C_2H_5)-CH_2-CH(C_2H_5)-CH_2-$ | $n_D^{25}$: | 1.5003 | |
| $H_3CO-CH_2-CH_2$ | $H_3CO-CH_2-CH_2-$ | b.p.: | 132° C./0.4 | mbar |
| $H_3CO-CH_2-CH(CH_3)-$ | $CH_3$ | b.p.: | 105° C./0.53 | mbar |
| $H_3CO-CH_2-CH(CH_3)-$ | $i-C_3H_7$ | b.p.: | 104° C./0.67 | mbar |
| 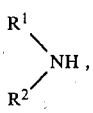 | $-CH_2-C\equiv CH$ | m.p.: | 73–75° C. | |
| tert.-$C_4H_9$ | $-CH_2-C\equiv CH$ | $n_D^{25}$: | 1.4950 | |
| $i-C_3H_7$ | 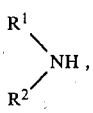 | $n_D^{25}$: | 1.4936 | |
| $C_6H_{11}$ | 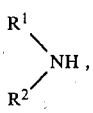 | m.p.: | 104–106° C. | |

-continued

| | | | | | | | | |
|---|---|---|---|---|---|---|---|---|
| $C_6H_{11}$ | | | | | —$CH_2$—CN | | | m.p.: 98–103° C. |
| $C_2H_5$—$CH(CH_3)$— | | | | | —$CH_2$—CN | | | $n_D^{25}$: 1.5028 |
| tert.-$C_4H_9$ | | | | | —$CH_2$—CN | | | m.p.: 117–119° C. |
| | | | | | —$CH_2$—CH——CH—$CH_2$—<br>\\ /<br>$(CH_2)_2$ | | | b.p.: 110–112° C./0.013 mbar |

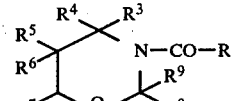

| R | $R^3$ | $R^4$ | $R^5$ | $R^6$ | $R^7$ | $R^8$ | $R^9$ | m.p./b.p./$n_D^{25}$ |
|---|---|---|---|---|---|---|---|---|
| $CH_2Cl$ | $CH_3$ | $CH_3$ | H | H | H | H | H | b.p.: 90° C./0.067 mbar |
| $CHCl_2$ | $CH_3$ | $CH_3$ | H | H | H | H | H | m.p.:108° C. |
| $CHCl_2$ | $CH_3$ | $CH_3$ | H | H | H | $CH_3$ | H | oil |
| $CHCl_2$ | $CH_3$ | $CH_3$ | H | H | $CH_3$ | H | H | m.p.:56° C. |
| $CHCl_2$ | $CH_3$ | $CH_3$ | H | H | $CH_3$ | $CH_3$ | H | 1.4918 |
| $CHCl_2$ | $CH_3$ | $CH_3$ | H | H | $CH_3$ | $C_2H_5$ | H | 1.4949 |
| $CHCl_2$ | $CH_3$ | $CH_3$ | H | H | $CH_3$ | $n$-$C_3H_7$ | H | 1.4915 |
| $CHCl_2$ | $CH_3$ | $CH_3$ | H | H | $CH_3$ | $i$-$C_3H_7$ | H | 1.4945 |
| $CHCl_2$ | H | H | $CH_3$ | $CH_3$ | H | H | H | m.p.:64° C. |
| $CHCl_2$ | H | H | $CH_3$ | $CH_3$ | H | $CH_3$ | H | m.p.:80° C. |
| $CHCl_2$ | H | H | $CH_3$ | $CH_3$ | H | $i$-$C_3H_7$ | H | m.p.:84° C. |
| $CHCl_2$ | $CH_3$ | $CH_3$ | H | H | $CH_3$ | CH-n$C_4H_9$<br>\|<br>$C_2H_5$ | H | 1.4849 |
| $CHCl_2$ | $CH_3$ | $CH_3$ | H | H | $CH_3$ | H | $CH(OCH_3)_2$ | oil |
| $CHCl_2$ | $CH_3$ | $CH_3$ | H | H | $CH_3$ | $CH_3$ | $CH_3OCH_2$ | oil |
| $CHCl_2$ | $CH_3$ | $CH_3$ | H | H | $CH_3$ | —$(CH_2)_4$— | | oil |
| $CHCl_2$ | $CH_3$ | $CH_3$ | H | H | $CH_3$ | —$(CH_2)_5$— | | oil |
| $CCl_3$ | $CH_3$ | $CH_3$ | H | H | H | H | H | m.p.:103° C. |
| $CHCl_2$ | $CH_3$ | $CH_3$ | H | H | H | $C_2H_5$ | H | 1.5152 |
| $CHCl_2$ | $CH_3$ | $CH_3$ | H | H | H | $n$-$C_3H_7$ | H | 1.5010 |

Ethyl-N-ethyl-N-bicyclo-[2.2.1]-hept-2-yl-thiolcarbamate may be obtained by reaction of ethyl-bicyclo-[2.2.1]-hept-2-yl-amine with ethylthiol chloroformate in the presence of an acid-binding agent.

The herbicidal active ingredients and the antagonistic compounds may be incorporated into the soil either together or separately and before or after sowing. They may also be applied, either separately or together, to the surface of the field to be treated, before or after sowing, but before emergence of the crop plants. The active ingredient and antagonist may be suspended, emulsified or dissolved in a spray liquor or may be in granular form, and may be formulated together or separately. It is also feasible to treat the seed with the antagonist before sowing. The herbicidal active ingredient is then applied on its own in the usual manner.

The ratio of thiolcarbamate to haloacylamide may, whether applied separately or together, vary within a wide range; it is normally from 1:1 to 1:0.01 parts by weight.

The new herbicidal agents may contain, in addition to thiolcarbamate and antagonist, other herbicidal or growth-regulating active ingredients of different chemical structure, e.g., 2-chloro-4-ethylamino-6-isopropylamino-1,3,5-triazine, without the antagonistic effect being impaired.

The agents according to the invention, or, when applied separately, the herbicidal active ingredients and the antidote are applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the herbicidal active ingredient and/or antidote, as such or dissolved in an oil or solvent, may be homogenized in water by means of wetting or dispersing agents, adherents or emulsifiers. Concentrates which are suitable for dilution with water may be prepared from herbicidal active ingredient and/or antidote, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of herbicidal active ingredient and/or antidote. Application rates are from 0.2 to 5 kg of herbicidal active ingredient per hectare. This amount of herbicidal active ingredient is applied, together or separately, with such an amount of antidote to give a ratio of herbicidal active ingredient to antagonistic compound of from 1:1 to 1:0.01 parts by weight.

Examples of formulations are given below.

I. 40 parts by weight of a mixture of 6 parts by weight of ethyl-N-ethyl-N-bicyclo-[2.2.1]-hept-2-yl-thiolcarbamate and 1 part by weight of N-dichloroacetyl-2,2-dimethyltetrahydro-1,3-oxazine is intimately mixed with 10 parts of the sodium salt of a phenolsulfonic acid-urea-formaldehyde condensate, 2 parts of silica gel and 48 parts of water. A stable aqueous dispersion is obtained. Dilution in 100,000 parts by weight of water gives an aqueous dispersion containing 0.04 wt% of the mixture of active ingredient+antidote.

II. 3 parts by weight of a mixture of 3 parts by weight of ethyl-N-ethyl-N-bicyclo-[2.2.1]-hept-2-yl-thiolcarbamate and 1 part by weight of N-dichloroacetyl-4,4,6-trimethyltetrahydro-1,3-oxazine is intimately mixed with 97 parts by weight of particulate kaolin. A dust is obtained containing 3% by weight of the mixture of active ingredient+antidote.

III. 30 parts by weight of a mixture of 3 parts by weight of ethyl-N-ethyl-N-bicyclo-[2.2.1]-hept-2-yl-thiolcarbamate and 1 part by weight of N,N-diallyldichloroacetamide is intimately mixed with a mixture consisting of 92 parts by weight of powdered silica gel and 8 parts by weight of paraffin oil which has been sprayed onto the surface of this silica gel.

IV. 20 parts of a mixture of 6 parts by weight of ethyl-N-ethyl-N-bicyclo-[2.2.1]-hept-2-yl-thiolcarbamate and 1 part by weight of N-isopropyl-N-propargyldichloroacetamide is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The influence of the herbicidal agents according to the invention on the growth of Indian corn and unwanted plants is demonstrated in the following biological examples.

Plastic boxes 51 cm long, 32 cm wide and 6 cm deep were filled with loamy sand (pH:6) containing about 1.5% humus. Indian corn (Zea mays) was sown shallow, in rows, in this substrate. Echinochloa crus-galli and Alopecurus were scattered at random as unwanted plants. The non-sterilized soil also additionally contained viable weed seeds which contributed to the weed population. A field with crop plants growing in it and infested with weeds was thus simulated.

The active ingredients and antagonists were applied separately and in the mixtures given below. They were emulsified or suspended in water as vehicle and the liquor was sprayed through finely distributing nozzles onto the soil surface, either immediately after sowing or prior to emergence of the test plants. After sowing and treatment the boxes were sprinkler-irrigated and covered with transparent plastic hoods until the plants emerged. These measures ensured that the plants germinated and took root uniformly. The boxes were set up in the greenhouse at from 18° to 30° C.

These greenhouse experiments were monitored until 3 to 5 Indian corn leaves had developed. No more damage due to the herbicidal agents was to be expected after this stage.

The scale for assessing the action of the agents was 0 to 100, 0 denoting normal emergence and development of the plants, with reference to the untreated control, and 100 denoting non-germination or withering of the plants. It should be borne in mind here that, for instance in Indian corn, odd crippled or retarded plants may occur even under completely normal conditions and without any chemical treatment.

In the following table, A stands for ethyl-N-ethyl-N-bicyclo[2.2.1]-hept-2-yl-thiolcarbamate, B for N-isopropyl-N-propargyldichloroacetamide, and C for N-dichloroacetyl-4,4-dimethyltetrahydro-1,3-oxazine.

The results show that the tolerance of ethyl-N-ethyl-N-bicyclo-[2.2.1]-hept-2-yl-thiolcarbamate by the crop plant Indian corn is increased most considerably by means of antagonistic compounds of the formula I.

TABLE

Improvement in the tolerance of ethyl-N-ethyl-N-bicyclo-[2.2.1]-hept-2-yl-thiolcarbamate by Indian corn by means of antagonistic compounds; preemergence treatment in the greenhouse

| Herbicidal active ingredient | Antagonistic compound | Appln. rate kg/ha | Test plants and % damage | | |
|---|---|---|---|---|---|
| | | | Zea mays | Alopecurus myosuroides | Echinochloa crus galli |
| A | — | 3.0 | 20 | 98 | 96 |
| A | — | 6.0 | 25 | 98 | 98 |
| | C | 4.0 | 5 | — | 0 |
| | B | 2.0 | 0 | 0 | 0 |
| A | + C | 6.0 + 1.0 | 5 | — | 95 |
| | | 3.0 + 0.5 | 5 | — | 95 |
| A | + B | 6.0 + 3.0 | 5 | — | 98 |
| | | 6.0 + 2.0 | 2.5 | 98 | 98 |
| | | 6.0 + 1.0 | 5 | 100 | 97 |
| | | 3.0 + 0.5 | 0 | 99 | 97 |
| | | 3.0 + 0.25 | 2.5 | 98 | 98 |

We claim:
1. A herbicidal agent containing ethyl-N-ethyl-N-bicyclo-[2.2.1]-hept-2-yl-thiolcarbamate of the formula

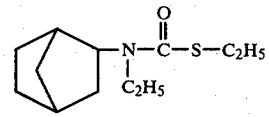

as herbicidal active ingredient and an effective amount of at least one haloacylamide antagonistic agent selected from the group consisting of N-isopropyl-N-propargyldichloroacetamide, N-dichloroacetyl-4,4-dimethyltetrahydro-1,3-oxazine, N-dichloroacetyl-4,4,6-trimethyltetrahydro-1,3-oxazine, and N,N-diallyldichloroacetamide.

2. A herbicidal agent as set forth in claim 1, wherein the antagonistic agent is N-isopropyl-N-propargyldichloroacetamide.

3. A herbicidal agent as set forth in claim 1, wherein the antagonistic agent is N-dichloroacetyl-4,4-dimethyltetrahydro-1,3-oxazine.

4. A herbicidal agent as set forth in claim 1, wherein the ratio of ethyl-N-ethyl-N-bicyclo[2.2.1]-hept-2-yl-thiolcarbamate to antagonistic agent, applied separately or together, is from 1:1 to 1:0.01 parts by weight.

5. A process for the selective control of unwanted plants, wherein a herbicidal agent as claimed in claim 1 is applied before, during or after sowing of the crop plants, or before or during emergence of the crop plants.

6. A process for the selective control of unwanted plants, wherein ethyl-N-ethyl-N-bicyclo-[2.2.1]-hept-2-yl-thiolcarbamate and an antagonistic compound selected from the group consisting of N-isopropyl-N-propargyldichloroacetamide, N-dichloroacetyl-4,4-dimethyl-tetrahydro-1,3-oxazine, N-dichloroacetyl-4,4,6-trimethyl-tetrahydro-1,3-oxazine, and N,N-diallyldichloroacetamide are applied, with or without incorporation, before, during or after sowing of the crop plants, or before or during emergence of the crop plants, either simultaneously or one after the other in any order.

7. A process as set forth in claims 5 or 6, wherein the crop plant is Indian corn.

* * * * *